(12) United States Patent
Bardey et al.

(10) Patent No.: US 8,815,814 B2
(45) Date of Patent: Aug. 26, 2014

(54) COSMETIC COMPOSITION CONTAINING OLIGOPEPTIDES

(75) Inventors: Vincent Bardey, Nancy (FR); Philippe Moussou, Tomblaine (FR); Christine Jeanmaire, Nancy (FR); Louis Danoux, Saulxures les Nancy (FR)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/643,659

(22) PCT Filed: Mar. 5, 2011

(86) PCT No.: PCT/EP2011/001099
§ 371 (c)(1),
(2), (4) Date: Oct. 26, 2012

(87) PCT Pub. No.: WO2011/134568
PCT Pub. Date: Nov. 3, 2011

(65) Prior Publication Data
US 2013/0108562 A1 May 2, 2013

(30) Foreign Application Priority Data
Apr. 29, 2010 (EP) .................................. 10161397

(51) Int. Cl.
| | | |
|---|---|---|
| *A61K 38/07* | (2006.01) | |
| *C07K 5/10* | (2006.01) | |
| *A61Q 19/00* | (2006.01) | |
| *A61Q 19/02* | (2006.01) | |
| *A61Q 19/08* | (2006.01) | |
| *C07K 5/103* | (2006.01) | |

(52) U.S. Cl.
CPC . *C07K 5/10* (2013.01); *A61K 38/07* (2013.01); *A61Q 19/00* (2013.01); *A61Q 19/02* (2013.01); *A61Q 19/08* (2013.01); *C07K 5/101* (2013.01)
USPC .......... 514/21.9; 514/17.2; 514/18.8; 530/330

(58) Field of Classification Search
CPC .......... C07K 5/10; C07K 5/101; A61K 38/07; A61Q 19/00; A61Q 19/02; A61Q 19/08
USPC ................. 514/21.9, 17.2, 18.8; 530/330
See application file for complete search history.

(56) References Cited

U.S. PATENT DOCUMENTS

| | | | | |
|---|---|---|---|---|
| 4,966,848 A | * | 10/1990 | Smith et al. ................. | 435/193 |
| 5,223,421 A | * | 6/1993 | Smith et al. ................. | 435/193 |
| 5,837,218 A | * | 11/1998 | Peers et al. .................. | 424/1.69 |
| 6,620,419 B1 | | 9/2003 | Lintner | |
| 6,974,799 B2 | | 12/2005 | Lintner | |

FOREIGN PATENT DOCUMENTS

| | | |
|---|---|---|
| DE | 19756377 | 6/1999 |
| FR | 2252840 | 6/1975 |
| GB | 1494915 | 11/1974 |
| JP | 10265400 | 10/1998 |
| WO | WO-2008/020954 | 2/2008 |
| WO | WO-2009/003034 | 12/2008 |
| WO | WO-2009/068351 | 6/2009 |

OTHER PUBLICATIONS

"Kosmetische Farbemittel", *Farbstoffkommission der Deutschen Forschungsgemeinschaft* Verlag Chemie, Weinheim 1984, pp. 81-106.
Hara, Yoshiaki et al., "Effect of Tetra-Peptide Isolated from Interleukin 1 (IL-1) on Corneal Epithelial Wound Healing in the Rabbit", *Exp. Eye Res*. 2001, pp. 107-113.
Lochhead, R.Y. et al., "Encyclopedia of Polymers and Thickeners for Cosmetics", *Cosmetics & Toiletries*, vol. 108, 1993, pp. 95-135.

* cited by examiner

*Primary Examiner* — Julie Ha
(74) *Attorney, Agent, or Firm* — Servilla Whitney LLC

(57) ABSTRACT

The invention is directed to the cosmetic use of tetrapeptides according to formula (I) $R_1$-Val-Leu-Leu-Lys-$R_2$ (I) wherein $R_1$ is linked to the NH2-terminal group of the peptide and is chosen from the group consisting of —H, a linear saturated or unsaturated or branched saturated or unsaturated acyl group having 1 to 24 carbon atoms, which may be functionalized by a —OH, —SH, —COOH or —$CONH_2$ group wherein $R_2$ is the terminal carboxylic group of the peptide either as —$COOR_3$ or —CO—$NH_2$, and wherein $R_3$ is chosen from the group consisting of —H, a linear saturated or unsaturated or branched saturated or unsaturated alkyl group having 1 to 24 carbon atoms, which may be functionalized by a —OH, —SH, —COOH or —$CONH_2$ group. The invention is also directed to the respective tetrapeptides and cosmetic compositions containing these.

20 Claims, No Drawings

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Specified tetrapeptide
<220> FEATURE:
<221> NAME/KEY: MISC_FEATURE
<222> LOCATION: (1)..(4)

<400> SEQUENCE: 1

Val Leu Leu Lys
1

<210> SEQ ID NO 2
<211> LENGTH: 4
<212> TYPE: PRT
<213> ORGANISM: Unknown
<220> FEATURE:
<223> OTHER INFORMATION: tetrapeptide
<220> FEATURE:
<221> NAME/KEY: MOD_RES
<222> LOCATION: (1)..(1)
<223> OTHER INFORMATION: N-palmitoyl

<400> SEQUENCE: 2

Gly Gln Pro Arg
1

<210> SEQ ID NO 3
<211> LENGTH: 4
<212> TYPE: PRT
<213> ORGANISM: Unknown
<220> FEATURE:
<223> OTHER INFORMATION: tetrapeptide

<400> SEQUENCE: 3

Val Leu Leu His
1
```

COSMETIC COMPOSITION CONTAINING OLIGOPEPTIDES

CROSS REFERENCE TO RELATED APPLICATIONS

This application is the National Phase entry of PCT/EP2011/001099, filed Mar. 5, 2011, which claims priority to European Patent Application 10161397.4, filed Apr. 29, 2010, the contents of which are incorporated herein by reference in their entirety.

FIELD OF THE INVENTION

The present invention relates to the cosmetic use of oligopeptides especially for anti-ageing compositions.

REFERENCE TO SEQUENCE LISTING

The material contained in the text file identified as "CGG029400US_ST25(2).txt," created Jan. 15, 2014 (817 bytes) is hereby incorporated by reference.

BACKGROUND OF THE INVENTION

Cosmetic compositions which are on the market today are known to improve the appearance of the skin. They are usually used to prevent or treat signs of skin ageing expressed as loss of firmness, decrease of skin thickness, fine lines, wrinkles, loss of elasticity, sagging, dryness, age spots, diminished rate of turnover, abnormal desquamation, decrease of the density and disorganization of the extra-cellular matrix in the dermis and other histological changes. It is well known that exposure to oxidative stress, UV rays, irritants, allergens, and various environmental toxins have an impact on these properties and accelerate skin ageing, so that cosmetic compositions are generally designated as anti-ageing compositions.

The skin consists of three layers, the epidermis, the dermis and the subcutaneous tissue (hypodermis), of which the dermis is composed of two distinct layers, the papillary and reticular dermis.

The skin's extra-cellular matrix is a complex network of macromolecules, such as collagen or elastic fibers, glycoproteins, glycosaminoglycans and proteoglycans. It provides a physical framework to assume mechanical strength and participates in cell metabolism regulation. In the dermis more than 70% of the proteins are collagens. Collagen is responsible for the skin's strength. It is produced by cells called fibroblasts, which are found scattered throughout the dermis. One major type of collagen in the human skin dermis is collagen type I, which forms the network of fibers.

The dermis also contains quantitatively minor collagens, such as collagen type XII and collagen type XIV, members of the FACIT (Fibril Associated Collagens with Interrupted Triple helices). FACITs are important for the good quality of the extra-cellular matrix. They are found associated with collagens fibers in the interfibrillar space and are involved in the correct structuring of the fiber network.

The other fibers composing the extra-cellular matrix of dermis are elastic fibers, mainly composed of tropoelastin that are polymerized on microfibrils. Elastic fibers are directly involved in the elastic property of the skin and are also produced by the fibroblasts in the skin dermis.

During skin ageing, the synthesis rate of collagen and elastin fibers decreases while their degradation level strongly increases. The result of these two ageing processes is a strong reduction of the amount of fibers in the dermis, inducing alterations of the skin properties.

The production of the extra-cellular matrix and of enzymes involved in its degradation is to a great extent controlled by fibroblasts and the balance between synthesis and degradation is fundamental for correct skin homeostasis. Some growth factors, such as transforming growth factors (TGF) or connective tissue growth factor (CTGF) are signals that strongly stimulate fibroblast growth and the production of the extra-cellular matrix.

The metabolism of the fibroblast is modified during ageing due to many factors. Alteration of the communication molecules, homeostasis or accumulation of altered proteins by reactive oxygen species (ROS) are some causes of this fibroblast metabolism modification. ROS can be produced by endogenous metabolism of cells, mainly in the mitochondria. In addition, ROS production may result from extrinsic factors such as UV exposure or pollution strongly oxidant. To fight against oxidative stress, cells have different systems to degrade endogenous or exogenous ROS, such as catalase or peroxidise. Cells also possess some defence systems to revert the ROS-induced modifications of proteins. For example, oxidized methionines can be reverted by the methionine sulfoxide reductases. These enzymes may be located in the different cell compartments. For example, glutaredoxin-2 is located either in nucleus or in mitochondria, the main localization of endogenous ROS production. Glutaredoxins and other proteins have the property to disrupt disulfide bridges induced by ROS. Nevertheless, these repair systems are also deteriorated during ageing.

Hence there is a need for effective protection of the skin against environmental influences.

Some cosmetic and dermopharmaceutical compositions containing oligopeptides are already on the market. Tripeptides such as N-palmitoyl-Gly-His-Lys (in Matrixyl® 3000 available from De Wolf Chemical, USA) palmitoyl-tripeptide-3 (SYN®-COLL by Pentapharm, Ltd. Switzerland) and tetrapeptides as N-palmitoyl-Gly-Gln-Pro-Arg (SEQ ID NO:2) (in Matrixyl® 3000 available from De Wolf Chemical, USA) are used in cosmetics due to their dermal stimulating properties. U.S. Pat. No. 6,974,799 is related to pharmaceutical, personal care and cosmetic compositions containing these oligopeptides useful for treating visible signs of ageing including wrinkles, stretch marks and dark circles.

Cosmetic or dermopharmaceutical compositions with peptides of the general sequence X-Thr-Thr-Lys-Y, wherein in particular X is lysine and Y is serine are used for healing, hydrating and improving skin appearance during natural or induced ageing (U.S. Pat. No. 6,620,419B).

Topical personal care and skin care compositions comprising an effective amount of a tetrapeptide selected from the group of tetrapeptides with the motif GX1X2G, PX1X2P, or PX1X2K; an effective amount of at least one additional active ingredient and a dermatologically acceptable carrier is object of the International application WO 2009/068351A. The peptides disclosed in WO2009/068351 act on collagen fibers present in the dermis both in quantity (COL1A1, COL1A2 gene expression and collagen production) and organization (FN1 gene expression) resulting in an increase of skin firmness and on hyaluronic acid production (HAS1 gene expression) increasing the hydration of the skin. The international application WO 2008/020954 discloses cosmetic compositions comprising dermal stimulating palmitoyl oligopeptides that regenerate the dermal matrix and a rapid acting muscle relaxant derived from the extract of the plant *Acemella oleracea*. By limiting cutaneous deformation caused by the contraction of facial muscles the extract increases the efficiency of the peptides in reducing expression lines.

Val-Leu-Leu-His (SEQ ID NO:3) tetrapeptide is a consensus sequence between human IL-1a and bovine parotine. It has been shown to stimulate proliferation of epithelial cells from rabbit cornea, and to exhibit a significant wound healing activity on injured rabbit cornea. (Hara et al., Exp Eye Res, 2001, 72, 107-13).

Aim of present invention was to provide a safe product for cosmetic skin treatment, in particular to improve the appearance of the skin and to improve skin elasticity resulting in body firming and to reduction of visible signs of ageing.

SUMMARY OF THE INVENTION

The present invention is related to tetrapeptides according to formula (I), cosmetic compositions containing tetrapeptide(s) according to formula (I), and their use to improve the appearance of the skin, skin elasticity, body firming and to reduce the visible signs of ageing.

DETAILED DESCRIPTION OF THE INVENTION

One embodiment of the current invention is directed to the cosmetic use of tetrapeptides according to formula (I)

$R_1$-Val-Leu-Leu-Lys-$R_2$            (I) SEQ ID NO:1 wherein $R_1$ is linked to the NH2-terminal group of the peptide and is chosen from the group consisting of —H, a linear saturated or unsaturated or branched saturated or unsaturated acyl group having 1 to 24 carbon atoms, which may be functionalized by a —OH, —SH, COOH or —CONH$_2$ group.

wherein $R_2$ is the terminal carboxylic group of the peptide either as —COOR$_3$ or —CO—NH$_2$, and wherein $R_3$ is chosen from the group consisting of —H, a linear saturated or unsaturated or branched saturated or unsaturated alkyl group having 1 to 24 carbon atoms, which may be functionalized by a —OH, —SH, —COOH or —CONH$_2$ group.

Preferably $R_1$ is selected from the group consisting of H, acetyl (CH$_3$—CO—), ethanoyl (CH$_3$—CH$_2$—CO—), propionyl, isopropionyl, butanoyl (=butyryl; CH$_3$—(CH$_2$)$_2$—CO—), isobutyryl, decanoyl, lauryl, myristyl, palmitoyl (CH$_3$—(CH$_2$)$_{14}$—CO—), stearoyl (CH$_3$—(CH$_2$)$_{16}$—CO—), oleyl, lipoyl, linoleyl or conjugated linoleyl, and $R_2$ is selected from the group consisting of CO—NH$_2$, COOR$_3$ wherein $R_3$ is selected from the group consisting of H, methyl, ethyl, propyl, isopropyl, butyl, isobutyl.

More preferably $R_1$ is selected from the group consisting of H, and acetyl and $R_2$ is selected from the group consisting of —COOH, and —CO—NH$_2$ In an embodiment, the amino terminal is not substituted but consists of an amino group. It is within the scope of the invention that, in case $R_1$=H, the tetrapeptide of the invention can be protonated, and be present as salt, e.g. as chloride, bromide, fluoride or iodide.

Most preferably $R_1$ is acetyl $R_2$ is —COOH.

It was found that the tetrapeptide(s) according to formula (I) improve the organization of the extra-cellular matrix in the dermis, stimulate the production of both collagens and elastin, and improve the cellular anti-oxidative defence of the skin. Hence they could especially be used as anti-ageing agents and for increasing skin elasticity.

Another embodiment of the current invention is directed to tetrapeptides according to formula (I)

$R_1$-Val-Leu-Leu-Lys-$R_2$            (I) SEQ ID NO:1 wherein $R_1$ is linked to the NH2-terminal group of the peptide and is chosen from the group consisting of —H, a linear saturated or unsaturated or branched saturated or unsaturated acyl group having 1 to 24 carbon atoms, which may be functionalized by a —OH, —SH, —COOH or —CONH$_2$ group, wherein $R_2$ is the terminal carboxylic group of the peptide either as —COOR$_3$ or —CO—NH$_2$, and wherein $R_3$ is chosen from the group consisting of —H, a linear saturated or unsaturated or branched saturated or unsaturated alkyl group having 1 to 24 carbon atoms, which may be functionalized by a —OH, —SH, —COOH or —CONH$_2$ group, preferably R1 is selected from the group consisting of H, acetyl (CH$_3$—CO—), ethanoyl (CH$_3$—CH$_2$—CO—), propionyl, isopropionyl, butanoyl (=butyryl; CH$_3$—(CH$_2$)$_2$—CO—), isobutyryl, decanoyl, lauryl, myristyl, palmitoyl (CH$_3$—(CH$_2$)$_{14}$—CO—), stearoyl (CH$_3$—(CH$_2$)$_{16}$—CO—), oleyl, lipoyl, linoleyl or conjugated linoleyl, and $R_2$ is selected from the group consisting of CO—NH$_2$, COOR$_3$ wherein $R_3$ is selected from the group consisting of H, methyl, ethyl, propyl, isopropyl, butyl, isobutyl.

More preferably $R_1$ is selected from the group consisting of H, and acetyl

—$R_2$ is selected from the group consisting of —COOH, and —CO—NH$_2$

In an embodiment, the amino terminal is not substituted but consists of an amino group. It is within the scope of the invention that, in case $R_1$=H, the oligopeptide of the invention can be protonated, and be present as salt, e.g. as chloride, bromide, fluoride or iodide.

Most preferably $R_1$ is acetyl $R_2$ is —COOH

Thus in an especially preferred embodiment of the invention the tetrapeptide according to formula (I) is N-Acetyl-Val-Leu-Leu-Lys-OH (SEQ ID NO: 1)

In case where $R_1$ is not =H the term "tetrapeptide derivative" would be a more precise term. As used in this description, the term "tetrapeptide" or "tetrapeptides" encompasses tetrapeptides as well as tetrapeptide derivatives as well as salts of the tetrapeptides as well as salts of the tetrapeptide derivatives. Such possible salts include sodium-, potassium-, acetate, trifluoroacetate salts.

The amino acids can either occur in the L, the D, or the DL form in the peptide. In a preferred embodiment of the invention the amino acids are all in L form.

Use of Tetrapeptides

It was found that tetrapeptides according to formula (I) improve the organization of the extra-cellular matrix in the dermis, stimulate the production of both collagens and elastin, increase the production of CTGF (Connective Tissue Growth Factor) and improve the cellular anti-oxidative defenses of the skin.

The specific tetrapeptides according to formula (I) act:
- on collagen fiber production (collagen production) and organization (COL12A1 and COL14A1 gene expression), which results in an increase of skin firmness
- on elastic fibers (ELN gene expression). This effect is very important to increase the quality of the second fiber network present in the skin, also altered with ageing, resulting in an increase of skin elasticity.
- on anti-oxydative defense (GLRX2 and MSRA gene expression). By the stimulation of anti-oxidative defenses the tetrapeptides limit the effects of ageing and the accumulation of oxidative damages.

The tetrapeptides and topical composition containing the tetrapeptides according to the invention are especially useful for producing a cosmetic composition, which can be used to improve the appearance of the skin, body firming and reduce the visible signs of ageing. In particular these cosmetic compositions are used to prevent and/or to diminish intrinsic and/or extrinsic skin ageing, to delay the outcome of wrinkles, to reduce the depth of installed wrinkles, to diminish the appearance of fine lines, to improve the skin roughness, to prevent and/or to diminish skin sagging, to improve biomechanical properties e.g. such as skin firmness, skin elasticity, to prevent and/or to diminish the appearance of age spots, to improve the skin's regenerative and renewal process, to help rejuvenation of the aged or stressed human skin.

The tetrapeptides and topical composition containing the tetrapeptides according to the invention may be also used to help skin to fight against external or environmental stresses, such as oxidative stress, UV rays, irritants, allergens, pollution and various environmental toxins.

They can be used to increase the synthesis of collagens in the dermis, in particular of collagen type I, collagen type XII and collagen Type XIV, to up-regulate the expression of tropoelastin in dermal tissues, to up-regulate the expression of cellular enzymes involved in antioxidant defense, in particular of glutaredoxin-2 or methionine sulfoxide reductase A, to up-regulate the expression of endogenous growth factors implied in skin homeostasis, such as Connective Tissue Growth Factor.

Hence the tetrapeptides according to the invention are especially useful for producing a cosmetic composition with anti-ageing properties, that has an effect on improving skin appearance, delaying or reducing appearance of wrinkles, increasing firmness and especially increasing skin elasticity.

Synthesis of Tetrapeptides

The tetrapeptides according to the invention can be obtained by chemical or enzymatic synthesis. They can also be obtained by controlled hydrolysis of natural proteins of micro-organisms, plants or animals which contain the tetrapeptides or precursors of the tetrapeptides according to the invention.

The chemically or enzymatically obtained tetrapeptides can then be further derivatized (e.g. acetylated) by known chemical or enzymatic techniques to obtain the tetrapeptides according to the invention.

The tetrapeptides can also be produced by micro-organisms, which either naturally form the tetrapeptides, or have possibly been genetically modified or manipulated in some other way during fermentation through fermentation conditions such that they form the tetrapeptides according to the invention.

In case the tetrapeptides (or their precursors) are obtained by hydrolysis of proteins, the thus obtained tetrapeptides may be used crude, or may be further purified by known techniques (membrane filtration, chromatography, immunoprecipitation) to obtain the desired tetrapeptides.

Cosmetic Compositions Comprising Tetrapeptides

One embodiment of the invention is directed to cosmetic compositions comprising at least one tetrapeptide of the according to formula (I).

The tetrapeptide are preferably used in a concentration from 0.001 to 1000 ppm, preferably 0.05 to 500 ppm, more preferably from 0.5 to 100 ppm.

The tetrapeptides are preferably dissolved or solubilized in one or more solvents which are approved for cosmetic preparations, such as, for example, water, glycerol, propylene glycol, butylene glycol, pentylene glycole, ethoxylated or propoxylated diglycols, ethanol, propanol, isopropanol or mixtures of said solvents. Furthermore, it is possible to use the tetrapeptides solubilized in liposomes or adsorbed to organic polymers, or mineral supports or similar material which is acceptable for topical application.

Besides the solvents, further auxiliaries and additives may also be present in the preparations which are used according to the invention.

Cosmetic Compositions

The tetrapeptides and the cosmetic uses according to the invention can serve for producing cosmetic compositions, such as, for example, hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, tyrosinase inhibitors (depigmentation agents), hydrotropes, solubilizers, preservatives, perfume oils, dyes and the like.

Surfactants

Surface-active substances which may be present are anionic, nonionic, cationic and/or amphoteric or zwitterionic surfactants, the content of which in the compositions is usually about 1 to 70% by weight, preferably 5 to 50% by weight and in particular 10 to 30% by weight. Typical examples of anionic surfactants are soaps, alkylbenzenesulphonates, alkanesulphonates, olefinsulphonates, alkyl ether sulphonates, glycerol ether sulphonates, $\alpha$-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants comprise polyglycol ether chains, these can have a conventional homologue distribution, but preferably have a narrowed homologue distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds.

Typical examples of particularly suitable mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

Oil Bodies

Suitable oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes.

Emulsifiers

Suitable emulsifiers are, for example, nonionogenic surfactants from at least one of the following groups:

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogues thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan dihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COON or —SO$_3$H group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Consistency Regulators and Thickeners

Suitable consistency regulators are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligo-glucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminium and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat®L/Grünau), quaternized wheat polypeptides, polyethyleneimine, cationic silicone polymers, such as, for example, amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamidemethyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethyl-siloxane units and hydrogenated silicates.

UV Photoprotective Filters

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:
  3-benzylidenecamphor or 3-benzylidenenorcamphor and derivatives thereof, e.g. 3-(4-methylbenzylidene)camphor;
  4-aminobenzoic acid derivatives, preferably 2-ethylhexyl 4-(dimethylamino)benzoate, 2-octyl 4-(dimethylamino)benzoate and amyl 4-(dimethylamino)benzoate;
  esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenyl-cinnamate (octocrylene);
  esters of salicylic acid, preferably 2-ethylhexyl salicylate, 4-isopropylbenzyl salicylate, homomethyl salicylate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably di-2-ethylhexyl 4-methoxybenzalmalonate;
  triazine derivatives, such as, for example, 2,4,6-trianilino (p-carbo-2'-ethyl-1'-hexyloxy)-1,3,5-triazine and octyltriazone or dioctylbutamidotriazone (Uvasorb® HEB);
  propane-1,3-diones, such as, for example, 1-(4-tert-butylphenyl)-3-(4'-methoxyphenyl)propane-1,3-dione;
  ketotricyclo(5.2.1.0)decane derivatives.

Suitable water-soluble substances are:
  2-phenylbenzimidazole-5-sulphonic acid and the alkali metal, alkaline earth metal, ammonium, alkylammonium, alkanolammonium and glucammonium salts thereof;
  sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid and 2-methyl-5-(2-oxo-3-bornyl-idene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

Biogenic Active Ingredients and Antioxidants

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydro-guaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Deodorants and Antimicrobial Agents

Cosmetic deodorants counteract, mask or remove body odours. Body odours arise as a result of the effect of skin bacteria on apocrine perspiration, with the formation of degradation products which have an unpleasant odour. Accordingly, deodorants comprise active ingredients which act as antimicrobial agents, enzyme inhibitors, odour absorbers or odour masking agents.

Antimicrobial Agents

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl) urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1)-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odour. Other substances which are suitable esterase inhibitors are sterol sulphates or phosphates, such as, for example, lanosterol, cholesterol, campesterol, stigmasterol and sitosterol sulphate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers

Suitable odour absorbers are substances which are able to absorb and largely retain odour-forming compounds. They lower the partial pressure of the individual components, thus also reducing their rate of diffusion. It is important that in this process perfumes must remain unimpaired. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl sali-cylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
nonionic emulsifiers,
coemulsifiers,
consistency regulators,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium penta-chlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

anti-inflammatory, skin-protective or perfumed essential oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

Insect Repellents

Suitable insect repellents are N,N-diethyl-m-toluamide, 1,2-pentanediol or ethyl butylacetylaminopropionate.

Self-Tanning Agents and Depigmentation Agents

A suitable self-tanning agent is dihydroxyacetone. Suitable tyrosinase inhibitors, which prevent the formation of melanin and are used in depigmentation agents, are, for example, arbutin, ferulic acid, kojic acid, coumaric acid and ascorbic acid (vitamin C).

Hydrotropic Agents

To improve the flow behaviour, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1,3-propanediol.

Preservatives

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

Perfume Oils and Aromas

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzyl-carbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable aromas are, for example, peppermint oil, spearmint oil, anise oil, star anise oil, caraway oil, eucalyptus oil, fennel oil, lemon oil, wintergreen oil, oil of cloves, menthol and the like.

Dyes

Dyes which can be used are the substances which are approved and suitable for cosmetic purposes, as are summarized, for example, in the publication "Kosmetische Farbemittel" [Cosmetic Colorants] from the Farbstoffkommission der Deutschen Forschungsgemein-schaft [Dyes Commission of the German Research Council], Verlag Chemie, Weinheim, 1984, pp. 81-106. Examples are cochineal red A (C.I.16255), patent blue V (C.I.42051), indigotin (C.I.73015), chlorophyllin (C.I.75810), quinoline yellow (C.I.47005), titanium dioxide (C.I.77891), indanthrene blue RS (C.I.69800) and madder lake (C.I.58000). As a luminescent dye, it is also possible for luminol to be present. These dyes are customarily used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

EXAMPLES

Example 1

Cosmetic Emulsion

| Trade name | INCI | % by weight |
|---|---|---|
| Emulgade ® SE-PF[2] | Glyceryl Stearate (and) Ceteareth-20 (and) Ceteareth-12 (and) Cetearyl Alcohol (and) Cetyl palmitate | 6.00 |
| Lanette ® O[2] | Cetearyl Alcohol | 2.50 |
| Cegesoft ® C24[2] | Ethyl hexyl palmitate | 6.00 |
| Cetiol ® PGL[2] | Hexyldecanol (and) Hexyldecyl laurate | 5.00 |
| Myritol ® 312[2] | Caprylic/Capric Trigylceride | 3.00 |
| DC 200-50cts[3] | Dimethicone | 1.00 |
| Deionized water | | add 100 |
| Keltrol T[4] | Xantham Gum | 0.20 |
| Elestab 50J[1] | Chlorphenesin (and) Methylparaben | 0.40 |
| Glycerine | | 4.00 |
| Carbopol 980[5] 2% | Carbomer | 15.00 |
| NaOH 10% | | 0.60 |
| Perfume ChampalineG10415611[6] | | 0.10 |
| Tetrapeptide | Acetyl-Val-Leu-Leu-Lys (SEQ ID NO: 1) | 0.0003 |

Suppliers
[1]Laboratoires Sérobiologiques;
[2]Cognis;
[3]Dow Corning;
[4]Kelco;
[5]Noveon,
[6]Robertet

Example 2

Effect of Acetyl-Val-Leu-Leu-Lys (SEQ ID NO:1) on Type I collagen

The peptide Acetyl-Val-Leu-Leu-Lys (SEQ ID NO:1)was incubated on human dermal fibroblasts cultured in vitro and the expression of the collagen type I was measured using an immunocytochemistry (ICC) method.

The human dermal fibroblasts were cultured within growth medium enriched with Foetal Calf Serum (FCS) at 10% and incubated for 2 days at 37° C. Then the growth medium was exchanged for a standard medium containing sodium ascorbyl at 5 µg/ml with FCS at 1% and with or without the Acetyl-Val-Leu-Leu-Lys (SEQ ID NO:1)peptide at 5.1 µg/ml. A positive control condition with sodium ascorbyl at 20 µg/ml was performed. Cells were incubated for 72 hours at 37° C. with the peptide. Cultured human dermal fibroblasts were fixed by acetone for 10 minutes at −20° C. and incubated for 1 hour at room temperature with a primary antibody against collagen type I [Abcam] diluted at 1/250. Fluorescein isothiocyanate (FITC) labelled secondary antibody [Clini-Sciences, France] was used for revelation. The obtained immuno-staining was observed using a confocal laser scanning microscope [TCS SPE, Leica, France] and quantified by an image analyzer [Quantimet Q5001W, Leica, France]. The staining occupation was evaluated. The results were presented as a mean +/−SEM (Standard Error of Mean) from 6 measures.

TABLE 1

Stimulating effect of Acetyl-Val-Leu-Leu-Lys (SEQ ID NO: 1) on collagen type I detected by immuno-staining

| | % of staining occupation |
|---|---|
| Control | 10.68 +/− 1 |
| Sodium ascorbyl at 20 µg/ml | 18.01 +/− 1.07 (**) |
| Acetyl-Val-Leu-Leu-Lys (SEQ ID NO: 1) at 5.1 µg/ml | 31.07 +/− 2.22 (**) |

Statistics: Mann & Whitney test: (**) = very significant effect (p < 0.01).

Acetyl-Val-Leu-Leu-Lys (SEQ ID NO:1) peptide has significantly increased the level of collagen type I. This effect is superior to the stimulation effect of the sodium ascorbyl at 20 µg/ml.

Example 3

Effect of Acetyl-Val-Leu-Leu-Lys (SEQ ID NO:1)on the Level of COL14A1 mRNAs

The peptide Acetyl-Val-Leu-Leu-Lys (SEQ ID NO:1) was incubated on human dermal fibroblasts cultured in vitro and the expression of the collagen type XIV gene (COL14A1) was measured using a quantitative reverse-transcription and polymerase chain reaction (qRT-PCR) method.

The human dermal fibroblasts were cultured within growth medium enriched with FCS at 10% and incubated for 1 day at 37° C. Then the growth medium was exchanged for a standard medium without FCS but with or without the Acetyl-Val-Leu-Leu-Lys (SEQ ID NO:1) peptide at 1.0 µg/ml. Cells were then incubated for 24 hours, 48 hours or 72 hours at 37° C. before extraction of total RNA. The level of COL14A1 mRNAs in the different conditions was evaluated comparatively to the level of EEF1A1 mRNA as housekeeping gene (qRT-PCR method) for each condition.

The results were calculated through the level of COL14A1 mRNA measured in the control condition (without peptide treatment) for the different incubation times as 100% and presented as a mean+/−SEM from 3 or 5 assays in duplicate.

TABLE 2

Effect of Acetyl-Val-Leu-Leu-Lys (SEQ ID NO: 1) on collagen type XIV gene detected by qRT-PCR

| | Treatment duration | | |
|---|---|---|---|
| | 24 hours | 48 hours | 72 hours |
| Control | 100 +/− 0 | 100 +/− 0 | 100 +/− 0 |
| Acetyl-Val-Leu-Leu-Lys (SEQ ID NO: 1) at 1.0 µg/ml | 175 +/− 23 (*) | 220 +/− 32 (*) | 213 +/− 27 (*) |

Statistics: Mann & Whitney test: (*) = significant effect (p < 0.05)

Acetyl-Val-Leu-Leu-Lys (SEQ ID NO:1) peptide has specifically and significantly increased the level of COL14A1 gene expression. The stimulation is detected after 24 hours of treatment and maintained during 3 days.

Example 4

Effect of Acetyl-Val-Leu-Leu-Lys (SEQ ID NO:1) on the Level of ELN mRNAs

The peptide Acetyl-Val-Leu-Leu-Lys (SEQ ID NO:1) was incubated on human dermal fibroblasts cultured in vitro and the expression of the tropoelastin gene (ELN) was measured using a qRT-PCR method.

The human dermal fibroblasts were cultured within growth medium enriched with FCS at 10% and incubated for 1 day at 37° C. Then the growth medium was exchanged for a standard medium without FCS but with or without the Acetyl-Val-Leu-Leu-Lys (SEQ ID NO:1) peptide at 1.0 µg/ml. Cells were incubated for 24 hours, 48 hours or 72 hours at 37° C. before extraction of total RNA. The level of ELN mRNAs in the different conditions was evaluated comparatively to the level of EEF1A 1 mRNA as housekeeping gene (qRT-PCR method) for each condition. The results were calculated through the level of ELN mRNA measured in the control condition (without peptide treatment) as 100% and presented as a mean+/−SEM from 3 assays in duplicate.

TABLE 3

Effect of Acetyl-Val-Leu-Leu-Lys (SEQ ID NO: 1) on tropoelastin gene detected by qRT-PCR

| | Treatment duration | | |
|---|---|---|---|
| | 24 hours | 48 hours | 72 hours |
| Control | 100 +/− 0 | 100 +/− 0 | 100 +/− 0 |
| Acetyl-Val-Leu-Leu-Lys (SEQ ID NO: 1) at 1.0 µg/ml | 127 +/− 11 (*) | 143 +/− 10 (*) | 217 +/− 49 (*) |

Statistics: Mann & Whitney test: (*) = significant effect (p < 0.05).

Acetyl-Val-Leu-Leu-Lys (SEQ ID NO:1) peptide has specifically and significantly increased the level of ELN gene expression.

Example 5

Effect of Acetyl-Val-Leu-Leu-Lys (SEQ ID NO:1) on the Level of GLRX2 mRNAs

The peptide Acetyl-Val-Leu-Leu-Lys (SEQ ID NO:1) was incubated on human dermal fibroblasts cultured in vitro and the expression of the glutaredoxin-2 gene (GLRX2), involved in cellular anti-oxidative defenses) was measured using a qRT-PCR method.

The human dermal fibroblasts were cultured within growth medium enriched with FCS at 10% and incubated for 1 day at 37° C. Then the growth medium was exchanged for a standard medium without FCS with or without the Acetyl-Val-Leu-Leu-Lys (SEQ ID NO:1) peptide at 1.0 μg/ml. Cells were incubated for 6 hours at 37° C. before extraction of total RNA. The level of GLRX2 mRNAs was evaluated comparatively to the level of HPRT1 (hypoxanthine phosphoribosyltransferase 1) mRNA as housekeeping gene (qRT-PCR method) for each condition.

The results were calculated through the level of GLRX2 mRNA measured in the control condition (without peptide treatment) as 100% and presented as a mean +/−SEM from 3 assays in duplicated.

TABLE 4

Effect of Acetyl-Val-Leu-Leu-Lys (SEQ ID NO: 1) on glutaredoxin-2 gene detected by qRT-PCR:

|  | 6 hours |
| --- | --- |
| Control | 100 +/− 0 |
| Acetyl-Val-Leu-Leu-Lys (SEQ ID NO: 1) at 1.0 μg/ml | 145 +/− 20 (*) |

Statistics: Mann & Whitney test: * = significant effect ($p < 0.05$).

Acetyl-Val-Leu-Leu-Lys (SEQ ID NO:1) peptide has specifically increased the level of GLRX2 gene expression.

The invention claimed is:

1. Tetrapeptides according to formula (I)

R₁-Val-Leu-Leu-Lys-R₂     (I) (SEQ ID NO: 1)

wherein R₁ is linked to the NH₂-terminal group of the tetrapeptide and is selected from the group consisting of a linear saturated or unsaturated or branched saturated or unsaturated acyl group having 1 to 24 carbon atoms, optionally functionalized by a —OH, —SH, —COOH or —CONH₂ group, and wherein R₂ is a terminal carboxylic group of the tetrapeptide either as COOR$_S$ or —CO—NH₂, and wherein R₃ is selected from the group consisting of —H, and a linear saturated or unsaturated or branched saturated or unsaturated alkyl group having 1 to 24 carbon atoms, optionally functionalized by a —OH, —SH, —COOH or —CONH₂ group.

2. The tetrapeptides according to claim 1, wherein R₁ is selected from the group consisting of acetyl (CH₃—CO—), ethanoyl (CH₃—CH₂—CO—), propionyl, iso-propionyl, butanoyl (=butyryl; CH₃—(CH₂)₂—CO—), isobutyryl, decanoyl, lauryl, myristyl, palmitoyl (CH₃—(CH₂)₁₄—CO—), stearoyl (CH₃—(CH₂)₁₆—CO—), oleyl, lipoyl, linoleyl and conjugated linoleyl, and R₂ is selected from the group consisting of CO—NH₂, and COOR$_S$ wherein R₃ is selected from the group consisting of H, methyl, ethyl, propyl, isopropyl, butyl, and isobutyl.

3. A cosmetic composition comprising at least one tetrapeptide according to claim 1.

4. The composition according to claim 3, further comprising mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, tyrosinase inhibitors, hydrotropes, solubilizers, preservatives, perfume oils or dyes.

5. A cosmetic composition comprising at least one tetrapeptide according to claim 2.

6. The composition according to claim 5, further comprising mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, tyrosinase inhibitors, hydrotropes, solubilizers, preservatives, perfume oils or dyes.

7. The cosmetic composition according to claim 5 which comprises 0.001 to 1000 ppm of the tetrapeptides.

8. The cosmetic composition according to claim 7 which comprises 0.5 to 100 ppm of the tetrapeptides.

9. The cosmetic composition according to claim 5, further comprising one or more solvents approved for cosmetic preparations.

10. The cosmetic composition according to claim 5, wherein the tetrapeptides are solubilized in liposomes, or adsorbed to organic polymers or mineral supports.

11. The cosmetic composition according to claim 3 which comprises 0.001 to 1000 ppm of the tetrapeptides.

12. The cosmetic composition according to claim 11 which comprises 0.5 to 100 ppm of the tetrapeptides.

13. The cosmetic composition according to claim 3, further comprising one or more solvents approved for cosmetic preparations.

14. The cosmetic composition according to claim 3, wherein the tetrapeptides are solubilized in liposomes, or adsorbed to organic polymers or mineral supports.

15. A method for improving appearance of skin, comprising applying to skin a composition comprising tetrapeptides according to formula (I)

R₁-Val-Leu-Leu-Lys-R₂     (I) (SEQ ID NO: 1)

wherein R₁ is linked to the NH₂-terminal group of the tetrapeptide and is selected from the group consisting of a linear saturated or unsaturated or branched saturated or unsaturated acyl group having 1 to 24 carbon atoms, optionally functionalized by a —OH, —SH, —COOH or —CONH₂ group, and wherein R₂ is a terminal carboxylic group of the tetrapeptide either as COOR$_S$ or —CO—NH₂, and wherein R₃ is selected from the group consisting of —H, and a linear saturated or unsaturated or branched saturated or unsaturated alkyl group having 1 to 24 carbon atoms, optionally functionalized by a —OH, —SH, —COOH or —CONH₂ group.

16. A method for improving appearance of skin, comprising applying to skin a composition comprising tetrapeptides according to formula (I)

R₁-Val-Leu-Leu-Lys-R₂     (I) (SEQ ID NO: 1)

wherein R₁ is selected from the group consisting of acetyl (CH₃—CO—), ethanoyl (CH₃—CH₂—CO—), propionyl, isopropionyl, butanoyl (=butyryl; CH₃—(CH₂)₂—CO—), isobutyryl, decanoyl, lauryl, myristyl, palmitoyl (CH₃—(CH₂)₁₄—CO—), stearoyl (CH₃—(CH₂)₁₆—CO—), oleyl, lipoyl, linoleyl or conjugated linoleyl, and R₂ is selected from the group consisting of CO—NH₂, COOR$_S$ wherein R₃ is selected from the group consisting of H, methyl, ethyl, propyl, isopropyl, butyl, and isobutyl.

17. The method according to claim 15 wherein the composition is an anti-ageing agent or increases skin elasticity.

18. The method according to claim 16 wherein the composition is an anti-ageing agent or increases skin elasticity.

19. The method according to claim 15 wherein the composition
   a) improves organization of extra-cellular matrix in the dermis,
   b) stimulates production of collagens and elastin,
   c) increases production of CTGF (Connective Tissue Growth Factor),
   d) improves cellular anti-oxidative defences of the skin,
   e) increases levels of collagen type I, and/or
   f) increases gene expression of COL12A1 and/or COL14A1 and/or a tropoelastin gene (ELN) and/or a GLRX2 gene and/or a MSRA gene.

20. The method according to claim 16 wherein the composition
   a) improves organization of extra-cellular matrix in the dermis,
   b) stimulates production of collagens and elastin,
   c) increases production of CTGF (Connective Tissue Growth Factor),
   d) improves cellular anti-oxidative defences of the skin,
   e) increases levels of collagen type I, and/or
   f) increases gene expression of COL12A1 and/or COL14A1 and/or a tropoelastin gene (ELN) and/or a GLRX2 gene and/or a MSRA gene.

* * * * *